United States Patent [19]

Lauer et al.

[11] Patent Number: 4,988,818
[45] Date of Patent: Jan. 29, 1991

[54] SYNERGISTIC TRIAZOLE COMPOUNDS

[75] Inventors: Manfred Lauer, Ludwigshafen; Matthias Zipplies, Hirschberg; Hubert Sauter, Mannheim, all of Fed. Rep. of Germany; Barbara A. Moore, Pittsboro, N.C.; Dale R. Carlson, Hillsborough, N.C.; Paul S. Zorner, Durham, N.C.; Karl-Otto Westphalen, Speyer; Bruno Wuerzer, Otterstadt, both of Fed. Rep. of Germany

[73] Assignee: BASF Aktiengesellschaft, Ludwigshafen, Fed. Rep. of Germany

[21] Appl. No.: 418,225

[22] Filed: Oct. 6, 1989

[51] Int. Cl.$^5$ .................................. C07D 249/08
[52] U.S. Cl. .......................... 548/267.4; 548/266.6; 546/276
[58] Field of Search .............. 546/276; 548/267.4, 548/266.6

[56] References Cited
FOREIGN PATENT DOCUMENTS
291852 11/1988 European Pat. Off. ......... 548/267.4

Primary Examiner—Glennon H. Hollrah
Assistant Examiner—Patricia L. Morris
Attorney, Agent, or Firm—Keil & Weinkauf

[57] ABSTRACT

Triazole compounds I

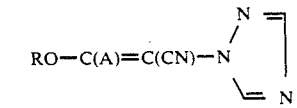

where A is $C_7$–$C_{20}$-alkyl or unsubstituted or substituted phenyl, naphthyl or pyridyl, and R is hydrogen or unsubstituted or substituted $C_1$–$C_6$-alkyl, $C_3$–$C_6$-alkenyl or $C_3$–$C_6$-alkynyl or is —$COR^x$ or —$SO_2R^x$, where $R^x$ is hydrogen or unsubstituted or substituted $C_1$–$C_8$-alkyl or phenyl, and their environmentally compatible salts, and herbicides containing one or more triazole compounds I, IA or IB

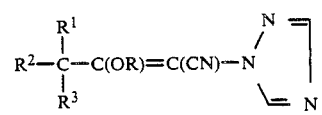

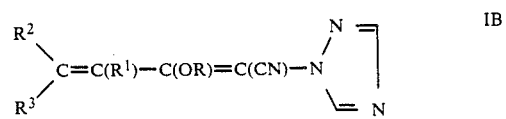

where $R^1$ is hydrogen, cyclopropyl or unsubstituted or substituted $C_1$–$C_6$-alkyl, $C_2$–$C_6$-alkenyl or $C_2$–$C_6$-alkynyl or is $C_1$–$C_4$-alkoxy, $C_2$–$C_4$-alkenyloxy or $C_2$–$C_4$-alkynyloxy, and $R^2$ and $R^3$ are each hydrogen, adamantyl or $C_1$–$C_3$-alkyl or, together with the carbon atom to which they are bonded, form unsubstituted or substituted $C_3$–$C_7$-cycloalkyl, $C_6$–$C_{10}$-bicycloalkyl, $C_6$–$C_{10}$-bicycloalkenyl, or their environmentally compatible salts and a benzothiadiazone.

2 Claims, No Drawings

SYNERGISTIC TRIAZOLE COMPOUNDS

The present invention relates to triazole compounds of the general formula I

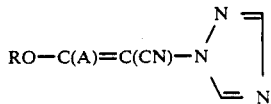

where A is $C_1$–$C_{20}$-alkyl or is phenyl, naphthyl or pyridyl, and these aromatic radicals may carry from one to five halogen atoms, a phenyl or phenoxy radical and/or from one to three of the following radicals: hydroxyl, nitro, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and/or $C_1$–$C_4$-haloalkylthio, R is hydrogen or is $C_1$–$C_6$-alkyl, $C_3$–$C_6$-alkenyl or $C_3$–$C_6$-alkynyl, and these groups may carry from one to five halogen atoms and/or one of the following radicals: $C_1$–$C_4$-alkoxy, $C_1$–$C_4$-haloalkoxy, $C_1$–$C_4$-alkylthio, $C_1$–$C_4$-haloalkylthio or phenyl; or is a radical $COR^x$ or a radical $SO_2R^x$, where $R^x$ is hydrogen or is $C_1$–$C_8$-alkyl which may carry from one to three halogen atoms or is phenyl which may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio, and their environmentally compatible salts, in particular those in which A is phenyl which may be monosubstituted to trisubstituted by halogen, $C_1$–$C_4$-alkyl and/or $C_1$- or $C_2$-haloalkyl, and herbicides which contain one or more of these triazole compounds I or one or more triazole compounds of the formula IA or IB

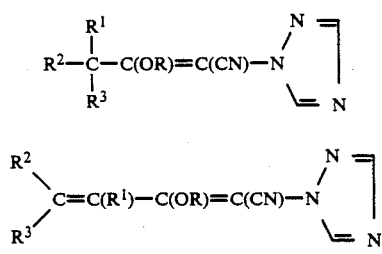

where R is hydrogen or cyclopropyl or is $C_1$–$C_4$-alkyl which may carry from one to five halogen atoms and/or from one to three of the following groups: hydroxyl, $C_1$–$C_4$-alkoxy, $C_2$–$C_4$-alkenyloxy or $C_2$–$C_4$-alkynyloxy, or is $C_2$–$C_6$-alkenyl or $C_2$–$C_6$-alkynyl, each of which may carry from one to five halogen atoms, or is $C_1$–$C_4$-alkoxy, $C_2$–$C_4$-alkenyloxy or $C_2$–$C_4$-alkynyloxy, $R^2$ and $R^3$ are each hydrogen, adamantyl or $C_1$–$C_3$-alkyl or, together with the carbon atom to which they are bonded, form a $C_3$–$C_7$-cycloalkyl group, a $C_6$–$C_{10}$-bicycloalkyl group or a $C_6$–$C_{10}$-bicycloalkenyl group, and these cyclic radicals may carry from one to three halogen atoms and/or $C_1$–$C_3$-alkyl groups, and R has the meanings stated in claim 1, or their environmentally compatible salts, and one or more herbicidal active ingredients from the group consisting of the benzothiadiazones of the formula II

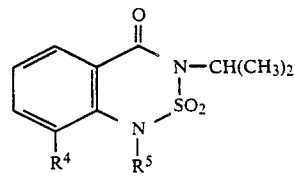

where $R^4$ is hydrogen, $C_1$–$C_4$-alkoxy or halogen and $R^5$ is hydrogen or cyano, and their environmentally compatible salts and conventional inert additives, and methods for selectively controlling undesirable plant growth with these herbicides.

EP-A-291 852 discloses the compounds IA and IB, defined above, as plant growth regulators.

Herbicidal active ingredients from the group consisting of the benzothiadiazones of the formula II

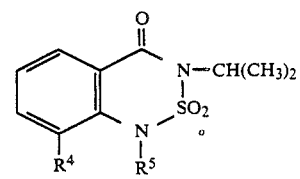

where $R^4$ is hydrogen, $C_1$–$C_4$-alkyl, $C_1$–$C_4$-alkoxy or halogen and $R^5$ is hydrogen or cyano, an their salts which are environmentally compatible and tolerated by crops are used for controlling undesirable plants (DE-A-15 42 836 and U.S. Pat. No. 4,158,559).

It is an object of the present invention to provide compounds which increase the action of the abovementioned herbicides II against undesirable plants in a superadditive manner without losing their toleration by crops. Such compounds are also referred to as synergistic agents.

We have found that this object is achieved by the triazole derivatives I defined at the outset. We have also found methods for the use of these compounds together with the known herbicides II for controlling undesirable plant growth. We have furthermore found that the triazole derivatives IA and IB defined above likewise have a synergistic action in conjunction with the herbicides II. The present invention therefore relates to agents which contain the compounds I, IA or IB and herbicides of type II, and methods for controlling undesirable plant growth with these agents, it being unimportant whether the herbicidal active ingredient and the synergistic compound are formulated and applied together or separately and, in the case of separate application, the order in which the herbicidal active ingredient and synergistic agent are applied being of no consequence.

The novel triazole derivatives I are obtainable in various ways.

For example, the compounds I in which R is hydrogen (referred to below as I') are preferably obtained by reacting an N-cyanomethylenetriazole III with a carbonyl halide IV in a conventional manner (EP-A-291 852) in an inert aprotic organic solvent in the presence of a base in accordance with the following equation:

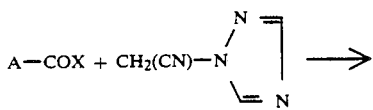

IV    III

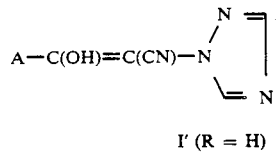

I' (R = H)

In formula IV, X is halogen, such as fluorine, chlorine or bromine, preferably chlorine or bromine, or the corresponding anhydride radical A—CO$_2$—.

The reaction can be carried out continuously or batchwise under atmospheric pressure or under pressures of up to 30 bar, preferably under atmospheric pressure of from 1 to 10 bar, and at from $-50°$ to $150°$ C., preferably from $-20°$ to $50°$ C.

Examples of suitable solvents are ethers, such as diethyl ether, methyl tert-butyl ether, tetrahydrofuran and dioxane, chlorohydrocarbons, such as methylene chloride, aromatic hydrocarbons, such as toluene and xylene, ketones, such as acetone, and alcohols, such as tert-butanol, and dimethyl formamide and dimethyl sulfoxide.

Examples of suitable bases are hydroxides of alkali metals and alkaline earth metals, such as sodium hydroxide, potassium hydroxide and calcium hydroxide, alcoholates of alkali metals and alkaline earth metals, such as sodium methylate, sodium ethylate, calcium methanolate or potassium tert-butylate, alkali metal of alkaline earth metals hydrides, such as sodium hydride, potassium hydride or calcium hydride, alkali metal or alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, and aromatic amines, such as pyridine or pyrrole.

In general, from 1 to 3, preferably from 1.9 to 2.2, mole equivalents, based on IV, of these bases are used. The molar ratio of educts III to IV is in general from 1.5:1 to 0.7:1, preferably from 1.3:1 to 0.8:1, in particular from 1.1:1 to 0.9:1. In particular, the reaction is carried out in tetrahydrofuran in the presence of from 1.9 to 2.2 mole equivalents of potassium tert-butylate as the base at from $-20$ to $30°$ C. under atmospheric pressure.

The compounds of the formula I in which R is not hydrogen (referred to below as I″) are obtained, for examples, by reacting a triazole compound I′ with an electrophilic reagent V in a conventional manner in an aprotic inert organic solvent in the presence of a base in accordance with the equation below.

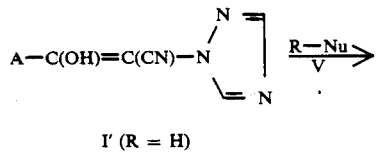

I' (R = H)

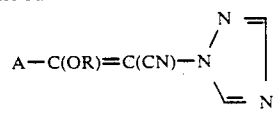

I″ (R ≠ H)

In formula V, Nu is a nucleophilic leaving group, such as halogen, preferably chlorine or bromine, or, if R is an acyl group —COR$^x$, also the corresponding anhydride radical R$^x$CO$_2$.

This reaction can be carried out continuously or batchwise, under atmospheric pressure or under pressures of up to 30 bar, preferably under atmospheric pressure or from 1 to 10 bar, and at from $-20°$ to $150°$ C., preferably from $20°$ to $100°$ C.

Where R is an acyl group —COR$^x$ or a sulfonyl group —SO$_2$R$^x$, suitable aprotic solvents are in particular nonpolar solvents such as the abovementioned ethers, in particular tetrahydrofuran. Suitable bases in this case are organic bases, such as alcoholates, in particular sodium methylate, sodium ethylate or potassium tert-butylate, and tertiary amines, in particular triethylamine and piperidine.

Where R is alkyl, alkenyl or alkynyl, aprotic polar solvents, such as cyclohexanone, acetone and acetonitrile, and the presence of inorganic bases, in particular potassium carbonate, are preferable for the reaction.

These bases are generally used in concentrations of from 0.5 to 1.5, preferably from 1 to 1 1, mole equivalents, based on the educt I′.

The molar ratio of the educts I′ to V is in general 2:1, preferably 1.5:1, in particular 1:1.

For the intended use of the compounds I as synergistic agents, suitable substituents are, for example, the following radicals:

R is hydrogen;

alkyl, such as methyl, ethyl, propyl, 1-methylethyl, butyl, 1-methylpropyl, 2-methylpropyl, 1,1-dimethylpropyl, pentyl, 2-methylbutyl, 3-methylbutyl, 2,2-dimethylpropyl, hexyl, 2-methylpentyl, 3-methylpentyl, 4-methylpentyl, 2,2-dimethylbutyl, 3,3-dimethylbutyl, 2,3-dimethylbutyl or 2-ethylbutyl;

alkenyl, such as allyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1,2-dimethyl-2-propenyl, 1,1-dimethyl-2-propenyl, 1-methyl-3-butenyl, 1-ethyl-2-propenyl, 2hexenyl, 1-methyl-2-pentenyl, 1-ethyl-2-butenyl or 2-ethyl-2-butenyl, preferably allyl or alkynyl, such as 2-propynyl, 2-butynyl, 3-butynyl, 1-methyl-2-propynyl, 1-methyl-2-butynyl, 1-ethyl-2-propynyl, 2-pentynyl, 3-pentynyl, 4-pentynyl or 1-methyl-2-pentynyl, preferably 2-propynyl, and these groups may carry from one to five halogen atoms, such as fluorine, chlorine or bromine and iodine, preferably fluorine and chlorine, and/or one of the following radicals alkoxy, such as methoxy, ethoxy, propoxy, 1-methylethoxy, butoxy, 1-methylpropyloxy, 2-methylpropyloxy and 1,1-dimethylethoxy, haloalkoxy, such as trifluoromethoxy, trichloromethoxy, fluoromethoxy, 2,2,2-trifluordethoxy, 1,2,2-trifluoromethoxy and 1,1,2,2-tetrafluoroethoxy, alkylthio, such as methylthio, ethylthio, propylthio, 2-propylthio, butylthio, 1-methylpropylthio, 2-methylpropylthio and 1,1-dimethylethylthio, haloalkylthio, preferably trifluoromethylthio and trichloromethylthio, or phenyl;

a radical COR$^x$ or a radical SO$_2$R$^x$, where R$^x$ is alkyl as stated for R, preferably methyl, which may carry from one to three halogen atoms, in particular fluorine, chlorine and bromine;

or phenyl which may carry from one to five halogen atoms, in particular fluorine and chlorine, and/or from one to three of the following radicals alkyl of one to four carbon atoms, as stated for R, in particular methyl, haloalkyl, such as chloromethyl, dichloromethyl, trichloromethyl, 1,1-dichloroethyl, 1-chloroethyl, fluoromethyl, difluoromethyl, trifluoromethyl, 2-fluoroethyl, 2,2-difluoromethyl and 2,2,2-trifluoroethyl; or alkoxy as stated above for R, in particular methoxy, haloalkoxy as stated above for R, in particular trifluoromethoxy, alkylthio as stated for R, in particular methylthio, or haloalkylthio as stated in particular for R, and A is alkyl of 7 to 20 carbon atoms which is preferably straight-chain or is branched at the chain end, such as heptyl, 5-methylhexyl, 4,4-dimethylpentyl, octyl, 6-methylheptyl, 5,5-dimethylhexyl, nonyl, 7-methyloctyl, 6,6-dimethylhepty, decyl, 8-methylnonyl, 7,7-dimethyloctyl, undecyl, 9-methyldecyl, 8,8-dimethylnonyl, dodecyl, 10-methylundecyl, 9,9-dimethyldecyl, tridecyl, 11-methyldodecyl, 10,10-dimethylundecyl, tetradecyl, 12-methyltridecyl, 11,11-dimethyldodecyl, pentadecyl, 13-methyltetradecyl, 12,12-dimethyltridecyl, hexadecyl, 14-methylpentadecyl, 13,13-dimethyltetradecyl, heptadecyl, 15-methylhexadecyl, 14,14-dimethylpentadecyl, octadecyl, 16-methylheptadecyl, 15,15-dimethylhexadecyl, nonadecyl, 17-methyloctadecyl, 16,16-dimethylheptadecyl, eicosyl, 18-methylnonadecyl and 17,17-dimethyloctadecyl, in particular straight-chain C$_7$–C$_{15}$-alkyl;

phenyl, naphthyl or pyridyl, where these aromatic radicals may carry from one to five halogen atoms, in particular fluorine and chlorine, a phenyl or phenoxy radical and/or from one to three of the following radicals hydroxyl, nitro, amino and alkyl, haloalkyl, alkoxy, haloalkoxy, alkylthio and haloalkylthio, as stated in general and in particular above for R$^x$, and their environmentally compatible salts with alkali metal or alkaline earth metal ions, such as lithium, sodium, potassium, magnesium and calcium, or with ammonium ions.

Some of the particularly preferred triazole compounds I are listed in the Table below.

TABLE

A—C(OR)=C(CN)—N(triazole)  I

| A | R |
|---|---|
| 1-napthyl | H |
| 2-napthyl | H |
| p-biphenyl | H |
| 3-pyridyl | H |
| 2-pyridyl | H |
| 4-pyridyl | H |
| phenyl | H |
| phenyl | CH$_3$ |
| phenyl | C$_2$H$_5$ |
| phenyl | n-C$_3$H$_7$ |
| phenyl | n-C$_4$H$_9$ |
| phenyl | n-C$_5$H$_{11}$ |
| phenyl | n-C$_6$H$_{13}$ |

TABLE-continued

A—C(OR)=C(CN)—N(triazole)  I

| A | R |
|---|---|
| phenyl | COCH$_3$ |
| phenyl | CO—C$_6$H$_5$ |
| phenyl | SO$_2$—CH$_3$ |
| phenyl | SO$_2$—C$_6$H$_5$ |
| phenyl | SO$_2$—C$_6$H$_4$—CH$_3$ |
| phenyl | CH$_2$—C$_6$H$_5$ |
| phenyl | CH$_2$CH=CH$_2$ |
| phenyl | Na$^+$ |
| phenyl | K$^+$ |
| phenyl | NH$_4^+$ |
| 2-F-phenyl | H |
| 2-F-phenyl | CH$_3$ |
| 2-F-phenyl | C$_2$H$_5$ |
| 2-F-phenyl | n-C$_3$H$_7$ |
| 2-F-phenyl | n-C$_4$H$_9$ |
| 2-F-phenyl | n-C$_5$H$_{11}$ |
| 2-F-phenyl | n-C$_6$H$_{13}$ |
| 2-F-phenyl | COCH$_3$ |
| 2-F-phenyl | CO—C$_6$H$_5$ |
| 2-F-phenyl | SO$_2$—CH$_3$ |
| 2-F-phenyl | SO$_2$—C$_6$H$_5$ |
| 2-F-phenyl | SO$_2$—C$_6$H$_4$—CH$_3$ |
| 2-F-phenyl | CH$_2$—C$_6$H$_5$ |
| 2-F-phenyl | CH$_2$CH=CH$_2$ |
| 2-F-phenyl | Na$^+$ |
| 2-F-phenyl | K$^+$ |
| 2-F-phenyl | NH$_4^+$ |
| 2-Cl-phenyl | H |
| 2-Cl-phenyl | CH$_3$ |
| 2-Cl-phenyl | C$_2$H$_5$ |
| 2-Cl-phenyl | n-C$_3$H$_7$ |

TABLE-continued $$A-C(OR)=C(CN)-N\begin{matrix}N=\\ \\ \end{matrix}\begin{matrix}\\ \\ N\end{matrix}$$  I

| A | R |
|---|---|
| 2-Cl-phenyl | n-C₄H₉ |
| 2-Cl-phenyl | n-C₅H₁₁ |
| 2-Cl-phenyl | n-C₆H₁₃ |
| 2-Cl-phenyl | COCH₃ |
| 2-Cl-phenyl | CO—C₆H₅ |
| 2-Cl-phenyl | SO₂—CH₃ |
| 2-Cl-phenyl | SO₂—C₆H₅ |
| 2-Cl-phenyl | SO₂—C₆H₄—CH₃ (p) |
| 2-Cl-phenyl | CH₂—C₆H₅ |
| 2-Cl-phenyl | CH₂CH=CH₂ |
| 2-Cl-phenyl | Na⁺ |
| 2-Cl-phenyl | K⁺ |
| 2-Cl-phenyl | NH₄⁺ |
| 2,4-Cl,Cl-phenyl | H |
| 2,4-Cl,Cl-phenyl | CH₃ |
| 2,4-Cl,Cl-phenyl | C₂H₅ |
| 2,4-Cl,Cl-phenyl | n-C₃H₇ |
| 2,4-Cl,Cl-phenyl | n-C₄H₉ |
| 2,4-Cl,Cl-phenyl | n-C₅H₁₁ |
| 2,4-Cl,Cl-phenyl | n-C₆H₁₃ |
| 2,4-Cl,Cl-phenyl | COCH₃ |
| 2,4-Cl,Cl-phenyl | CO—C₆H₅ |
| 2,4-Cl,Cl-phenyl | SO₂—C₆H₅ |
| 2,4-Cl,Cl-phenyl | SO₂—C₆H₄—CH₃ (p) |
| 2,4-Cl,Cl-phenyl | CH₂—C₆H₅ |
| 2,4-Cl,Cl-phenyl | CH₂CH=CH₂ |
| 2,4-Cl,Cl-phenyl | Na⁺ |
| 2,4-Cl,Cl-phenyl | K⁺ |
| 2,4-Cl,Cl-phenyl | NH₄⁺ |
| 2,6-Cl,Cl-phenyl | H |
| 2,6-Cl,Cl-phenyl | CH₃ |
| 2,6-Cl,Cl-phenyl | C₂H₅ |
| 2,6-Cl,Cl-phenyl | n-C₃H₇ |
| 2,6-Cl,Cl-phenyl | n-C₄H₉ |
| 2,6-Cl,Cl-phenyl | n-C₅H₁₁ |
| 2,6-Cl,Cl-phenyl | n-C₆H₁₂ |
| 2,6-Cl,Cl-phenyl | COCH₃ |
| 2,6-Cl,Cl-phenyl | CO—C₆H₅ |
| 2,6-Cl,Cl-phenyl | SO₂—C₆H₅ |
| 2,6-Cl,Cl-phenyl | SO₂—C₆H₄—CH₃ (p) |
| 2,6-Cl,Cl-phenyl | CH₂—C₆H₅ |
| 2,6-Cl,Cl-phenyl | CH₂CH=CH₂ |
| 2,6-Cl,Cl-phenyl | Na⁺ |
| 2,6-Cl,Cl-phenyl | K⁺ |
| 2,6-Cl,Cl-phenyl | NH₄⁺ |
| 3,5-Cl,Cl-phenyl | H |
| 3,5-Cl,Cl-phenyl | CH₃ |
| 3,5-Cl,Cl-phenyl | C₂H₅ |
| 3,5-Cl,Cl-phenyl | n-C₃H₇ |
| 3,5-Cl,Cl-phenyl | n-C₄H₉ |
| 3,5-Cl,Cl-phenyl | n-C₅H₁₁ |
| 3,5-Cl,Cl-phenyl | n-C₆H₁₂ |
| 3,5-Cl,Cl-phenyl | COCH₃ |
| 3,5-Cl,Cl-phenyl | CO—C₆H₅ |
| 3,5-Cl,Cl-phenyl | SO₂—C₆H₅ |
| 3,5-Cl,Cl-phenyl | SO₂—C₆H₄—CH₃ (p) |
| 3,5-Cl,Cl-phenyl | CH₂—C₆H₅ |
| 3,5-Cl,Cl-phenyl | CH₂CH=CH₂ |
| 3,5-Cl,Cl-phenyl | Na⁺ |
| 3,5-Cl,Cl-phenyl | K⁺ |
| 3,5-Cl,Cl-phenyl | NH₄⁺ |
| 2,4,6-trimethyl-phenyl | H |
| 2,4,6-trimethyl-phenyl | CH₃ |
| 2,4,6-trimethyl-phenyl | C₂H₅ |
| 2,4,6-trimethyl-phenyl | n-C₃H₇ |

TABLE-continued $$A-C(OR)=C(CN)-N\begin{array}{c}N=\\|\\=N\end{array}$$ I

| A | R |
|---|---|
| 2,4,6-trimethyl-phenyl | n-C$_4$H$_9$ |
| 2,4,6-trimethyl-phenyl | n-C$_5$H$_{11}$ |
| 2,4,6-trimethyl-phenyl | n-C$_6$H$_{12}$ |
| 2,4,6-trimethyl-phenyl | COCH$_3$ |
| 2,4,6-trimethyl-phenyl | CO—C$_6$H$_5$ |
| 2,4,6-trimethyl-phenyl | SO$_2$—C$_6$H$_5$ |
| 2,4,6-trimethyl-phenyl | SO$_2$—C$_6$H$_4$—CH$_3$ |
| 2,4,6-trimethyl-phenyl | CH$_2$—C$_6$H$_5$ |
| 2,4,6-trimethyl-phenyl | CH$_2$CH=CH$_2$ |
| 2,4,6-trimethyl-phenyl | Na$^+$ |
| 2,4,6-trimethyl-phenyl | K$^+$ |
| 2,4,6-trimethyl-phenyl | NH$_4^+$ |
| 3-Cl-phenyl | H |
| 4-Cl-phenyl | H |
| 2-Br-phenyl | H |
| 3-Br-phenyl | H |
| 4-Br-phenyl | H |
| 2-CF$_3$-phenyl | H |
| 2-CF$_3$-phenyl | n-C$_4$H$_9$ |
| 3-CF$_3$-phenyl | H |
| 4-CF$_3$-phenyl | H |
| 2-CH$_3$-phenyl | H |
| 2-CH$_3$-phenyl | Na |
| 2-CH$_3$-phenyl | n-C$_4$H$_9$ |
| 3-CH$_3$-phenyl | H |
| 4-CH$_3$-phenyl | H |
| 2-CH$_3$O-phenyl | H |
| 3-CH$_3$O-phenyl | H |
| 4-CH$_3$O-phenyl | H |
| 2,3-Cl,Cl-phenyl | H |
| 2,5-Cl,Cl-phenyl | H |
| 2-Cl,6-F-phenyl | H |
| 2-Cl,4-F-phenyl | H |
| 2-F,4-Cl-phenyl | H |
| 2,4-CH$_3$,CH$_3$-phenyl | H |
| 2,4-CH$_3$,CH$_3$-phenyl | n-C$_3$H$_7$ |
| 2,4-CH$_3$,CH$_3$-phenyl | n-C$_4$H$_9$ |
| 2,4-CH$_3$,CH$_3$-phenyl | n-C$_5$H$_{11}$ |
| 2,4-CH$_3$,CH$_3$-phenyl | n-C$_6$H$_{13}$ |
| 2,6-CH$_3$,CH$_3$-phenyl | H |
| (CH$_2$)$_9$—CH$_3$ | H |
| (CH$_2$)$_{14}$CH$_3$ | H |

In view of the intended use of compounds IA and IB as synergists for instance the following radicals are suitable substituents:

R$^1$ hydrogen; cyclopropyl;

alkyl as above for R$^x$, especially methyl which may bear one to three halogen atoms, such as in particular fluorine and chlorine and/or one to three of the following groups: hydroxy, alkoxy as above for R$^x$, especially methoxy and ethoxy; alkenyloxy such as ethenyloxy, 1-propenyloxy, 2-propenyloxy, 1-methyl-1-ethenyloxy 1-butenyloxy, 2-butenyloxy, 3-butenyloxy, 1-methyl-1-propenyloxy, 1-methyl-2-propenyloxy, 2-methyl-1-propenyloxy, 2-methyl-2-propenyloxy and 1-ethyl-1-ethenyloxy, 1-propynyloxy, 2-propynyloxy, 1-butynyloxy, 2-butynyloxy, 3-butynyloxy and 1-methyl-2-propynyloxy;

alkenyl such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-2-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl which may bear from one to five halogen atoms such as especially fluorine and chlorine; alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl which may bear from one to five halogen atoms such as especially fluorine and chlorine;

alkoxy as above for R$^x$, especially methoxy and ethoxy; alkenyloxy as generally mentioned above, or alkynyloxy as generally mentioned above;

R$^2$, R$^3$ hydrogen, adamantyl, especially 1-adamantyl; alkyl of one to three carbon atoms as mentioned above especially methyl and ethyl;

or—together with the carbon atom to which they are linked—cycloalkyl such as cyclopropyl, cyclobutyl, cyclopentyl, cyclohexyl and cycloheptyl, preferably cyclohexyl which mear bear from one to three of the following radicals: halogen such as especially fluorine and chlorine and/or alkyl such as especially methyl, bicycloalkyl such as especially bicyclo[2.2.1]heptanyl (norbornyl) bicyclo[2.2.2]octanyl and bicyclo[2.2.1-

]hexanyl or bicycloalkenyl such as especially bicyclo[2.2.1]hepten-3-yl, and these bicycles may bear from one to three of the following radicals: halogen such as especially chlorine and bromine and/or alkyl such as especially methyl and ethyl and R generally and in particular as mentioned above for the triazole derivatives I.

Specific triazole compounds IA and IB particularly preferred as synergists are given in Tables A and B below.

TABLE A $$R^2-\underset{R^3}{\overset{R^1}{\underset{|}{C}}}-C(OR)=C(CN)-N\begin{array}{c}N=\\ \diagup \\ \diagdown \\ N\end{array}\qquad IA$$

| $R^1$ | $R^2$ | $R^3$ | R |
|---|---|---|---|
| H | H | H | H |
| $CH_3$ | H | H | H |
| $C_2H_5$ | H | H | H |
| $CH_2=CH$ | H | H | H |
| $CH\equiv C$ | H | H | H |
| $CH_3CH_2CH_2$ | H | H | H |
| $(CH_3)_2CH$ | H | H | H |
| cyclopropyl | H | H | H |
| $CH_2=CHCH_2$ | H | H | H |
| $CH\equiv CCH_2$ | H | H | H |
| $CH_3CH_2CH_2CH_2$ | H | H | H |
| $(CH_3)_2CHCH_2$ | H | H | H |
| $CH_3CH(CH_3)CH_2$ | H | H | H |
| $(CH_3)_3C$ | H | H | H |
| $CH_2=CHCH_2CH_2$ | H | H | H |
| $CH\equiv CCH_2CH_2$ | H | H | H |
| $HOCH_2$ | H | H | H |
| $FCH_2$ | H | H | H |
| $ClCH_2$ | H | H | H |
| $CH_3O$ | H | H | H |
| $CH_3OCH_2$ | H | H | H |
| $CH_3CH_2OCH_2$ | H | H | H |
| $CH_2=CHCH_2OCH_2$ | H | H | H |
| $CH\equiv CCH_2OCH_2$ | H | H | H |
| $CH_3CH_2CH_2CH_2OCH_2$ | H | H | H |
| $CH_3$ | H | H | H |
| $C_2H_5$ | H | H | H |
| $CH_2=CH$ | H | H | H |
| $(CH_2)_5CH_3$ | H | H | H |
| $CH_3$ | $CH_3$ | H | H |
| $C_2H_5$ | $CH_3$ | H | H |
| $CH_2=CH$ | $CH_3$ | H | H |
| $CH\equiv C$ | $CH_3$ | H | H |
| $CH_3CH_2CH_2$ | $CH_3$ | H | H |
| $(CH_3)_2CH$ | $CH_3$ | H | H |
| cyclopropyl | $CH_3$ | H | H |
| $CH_2=CHCH_2$ | $CH_3$ | H | H |
| $CH\equiv CCH_2$ | $CH_3$ | H | H |
| $CH_3CH_2CH_2CH_2$ | $CH_3$ | H | H |
| $(CH_3)_2CHCH_2$ | $CH_3$ | H | H |
| $CH_3CH(CH_3)CH_2$ | $CH_3$ | H | H |
| $(CH_3)_3C$ | $CH_3$ | H | H |
| $CH_2=CHCH_2CH_2$ | $CH_3$ | H | H |
| $CH\equiv CCH_2CH_2$ | $CH_3$ | H | H |
| $HOCH_2$ | $CH_3$ | H | H |
| $FCH_2$ | $CH_3$ | H | H |
| $ClCH_2$ | $CH_3$ | H | H |
| $CH_3O$ | $CH_3$ | H | H |
| $CH_3OCH_2$ | $CH_3$ | H | H |
| $CH_3CH_2OCH_2$ | $CH_3$ | H | H |
| $CH_2=CHCH_2OCH_2$ | $CH_3$ | H | H |
| $CH\equiv CCH_2OCH_2$ | $CH_3$ | H | H |
| $CH_3CH_2CH_2CH_2OCH_2$ | $CH_3$ | H | H |
| $CH_3$ | $CH_3$ | $CH_3$ | H |
| $C_2H_5$ | $CH_3$ | $CH_3$ | H |
| $CH_2=CH$ | $CH_3$ | $CH_3$ | H |
| $CH\equiv C$ | $CH_3$ | $CH_3$ | H |
| $CH_3CH_2CH_2$ | $CH_3$ | $CH_3$ | H |
| $(CH_3)_2CH$ | $CH_3$ | $CH_3$ | H |
| cyclopropyl | $CH_3$ | $CH_3$ | H |
| $CH_2=CHCH_2$ | $CH_3$ | $CH_3$ | H |
| $CH\equiv CCH_2$ | $CH_3$ | $CH_3$ | H |
| $CH_3CH_2CH_2CH_2$ | $CH_3$ | $CH_3$ | H |
| $(CH_3)_2CHCH_2$ | $CH_3$ | $CH_3$ | H |
| $CH_3CH(CH_3)CH_2$ | $CH_3$ | $CH_3$ | H |
| $(CH_3)_3C$ | $CH_3$ | $CH_3$ | H |
| $CH_2=CHCH_2CH_2$ | $CH_3$ | $CH_3$ | H |

TABLE A-continued $$R^2-\underset{\underset{R^3}{|}}{\overset{\overset{R^1}{|}}{C}}-C(OR)=C(CN)-N-N\underset{N}{\overset{N}{\diagup}}\diagdown \quad IA$$

| R¹ | R² | R³ | R |
|---|---|---|---|
| CH≡CCH₂CH₂ | CH₃ | CH₃ | H |
| HOCH₂ | CH₃ | CH₃ | H |
| FCH₂ | CH₃ | CH₃ | H |
| ClCH₂ | CH₃ | CH₃ | H |
| CH₃O | CH₃ | CH₃ | H |
| CH₃OCH₂ | CH₃ | CH₃ | H |
| CH₃CH₂OCH₂ | CH₃ | CH₃ | H |
| CH₂=CHCH₂OCH₂ | CH₃ | CH₃ | H |
| CH≡CCH₂OCH₂ | CH₃ | CH₃ | H |
| CH₃CH₂CH₂CH₂OCH₂ | CH₃ | CH₃ | H |
| C₂H₅ | C₂H₅ | H | H |
| CH₂=CH | C₂H₅ | H | H |
| CH≡C | C₂H₅ | H | H |
| CH₃CH₂CH₂ | C₂H₅ | H | H |
| (CH₃)₂CH | C₂H₅ | H | H |
| CH₂=CHCH₂ | C₂H₅ | H | H |
| CH≡CCH₂ | C₂H₅ | H | H |
| CH₃CH₂CH₂CH₂ | C₂H₅ | H | H |
| (CH₃)₂CHCH₂ | C₂H₅ | H | H |
| CH₃CH(CH₃)CH₂ | C₂H₅ | H | H |
| C₂H₅ | C₂H₅ | CH₃ | H |
| CH₂=CH | C₂H₅ | CH₃ | H |
| CH≡C | C₂H₅ | CH₃ | H |
| CH₃CH₂CH₂ | C₂H₅ | CH₃ | H |
| CH₃CH₂CH₂CH₂ | C₂H₅ | CH₃ | H |
| C₂H₅ | C₂H₅ | C₂H₅ | H |
| CH₃CH₂CH₂ | CH₂CH₃ | C₂H₅ | H |
| CH₃CH₂CH₂CH₂ | CH₂CH₃ | C₂H₅ | H |
| CH₃CH₂CH₂ | n-C₃H₇ | H | H |
| CH₃CH₂CH₂ | n-C₃H₇ | CH₃ | H |
| CH₃CH₂CH₂ | n-C₃H₇ | CH₂CH₃ | H |
| CH₃CH₂CH₂ | n-C₃H₇ | n-C₃H₇ | H |
| H | —CH₂CH₂— | | H |
| CH₃ | —CH₂CH₂— | | H |
| H | —CH₂CH₂CH₂— | | H |
| CH₃ | —CH₂CH₂CH₂— | | H |
| H | —CH₂CH₂CH₂CH₂— | | H |
| CH₃ | —CH₂CH₂CH₂CH₂— | | H |
| H | —CH₂CH₂CH₂CH₂CH₂— | | H |
| CH₃— | —CH₂CH₂CH₂CH₂CH₂— | | H |
| H | adamantyl | H | H |
| CH₃ | adamantyl | H | H |
| C₂H₅ | C₂H₅ | H | COH |
| C₂H₅ | C₂H₅ | H | COCH₃ |
| C₂H₅ | C₂H₅ | H | COC₂H₅ |
| C₂H₅ | C₂H₅ | H | COCH₂CH₃ |
| C₂H₅ | C₂H₅ | H | COCH₂CH₂CH₂CH₃ |
| C₂H₅ | C₂H₅ | H | COC(CH₃)₃ |
| C₂H₅ | C₂H₅ | H | COCH(CH₃)CH₂CH₃ |
| C₂H₅ | C₂H₅ | H | COCH(C₂H₅)₂ |
| C₂H₅ | C₂H₅ | H | —CO—C₆H₅ |
| C₂H₅ | C₂H₅ | H | —CO—C₆H₄—Cl |
| C₂H₅ | C₂H₅ | H | —CO—C₆H₄—NO₂ |

TABLE A-continued $$R^2-\underset{R^3}{\overset{R^1}{C}}-C(OR)=C(CN)-N\diagup\overset{N=}{\underset{=N}{N}}\diagdown$$ IA

| R¹ | R² | R³ | R |
|---|---|---|---|
| C₂H₅ | C₂H₅ | H | 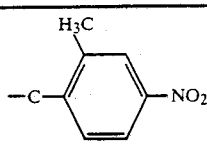 2-CH₃-4-NO₂-C₆H₃-C(=O)- |
| C₂H₅ | C₂H₅ | H | 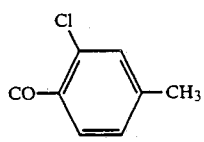 2-Cl-4-CH₃-C₆H₃-C(=O)- |
| CH₃ | C₂H₅ | H | CO—CH₃ |
| CH₃ | CH₃ | CH₃ | SO₂CH₃ |
| CH₃ | CH₃ | CH₃ | 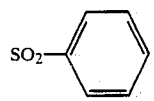 SO₂-C₆H₅ |
| CH₃ | CH₃ | CH₃ | 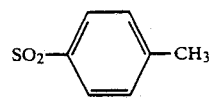 SO₂-C₆H₄-CH₃ |
| CH₃ | CH₃ | CH₃ | 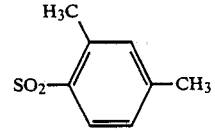 2-CH₃-4-CH₃-C₆H₃-SO₂- |
| H | CH₃ | C₂H₅ | SO₂CH₃ |
| H | CH₃ | C₂H₅ | 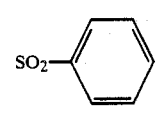 SO₂-C₆H₅ |
| H | CH₃ | C₂H₅ | 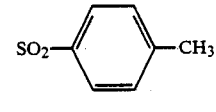 SO₂-C₆H₄-CH₃ |
| H | CH₃ | C₂H₅ | 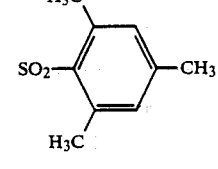 2,4,6-(CH₃)₃-C₆H₂-SO₂- |
| H | CH₃ | i-C₃H₇ | SO₂CH₃ |
| H | CH₃ | i-C₃H₇ | 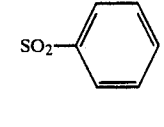 SO₂-C₆H₅ |
| H | CH₃ | i-C₃H₇ | 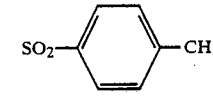 SO₂-C₆H₄-CH₃ |

TABLE A-continued
$$R^2-\underset{R^3}{\underset{|}{\overset{R^1}{\overset{|}{C}}}}-C(OR)=C(CN)-N\begin{array}{c}N=\\|\\N\end{array}\begin{array}{c}\\\\N\end{array}$$ IA
| $R^1$ | $R^2$ | $R^3$ | R |
|---|---|---|---|
| H | $CH_3$ | $i-C_3H_7$ | 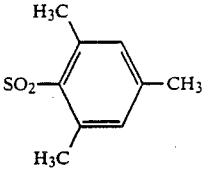 |
| H | $C_2H_5$ | $C_2H_5$ | $SO_2CH_3$ |
| H | $C_2H_5$ | $C_2H_5$ | 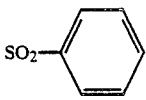 |
| H | $C_2H_5$ | $C_2H_5$ |  |
| H | $C_2H_5$ | $C_2H_5$ | 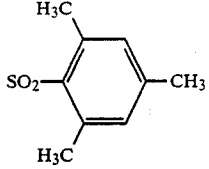 |
| H | $C_2H_5$ | $C_2H_5$ | 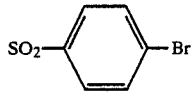 |
| H | $C_2H_5$ | $C_2H_5$ | 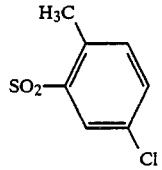 |
| H | $C_2H_5$ | $C_2H_5$ | 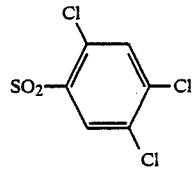 |
| H | $C_2H_5$ | $C_2H_5$ | 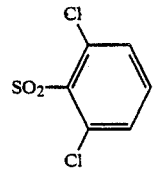 |
| H | 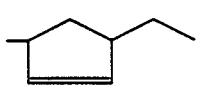 | | H |
| $CH_3$ | 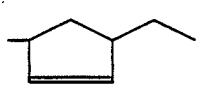 | | H |

TABLE A-continued

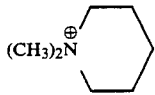

IA

| R¹ | R² | R³ | R |
|---|---|---|---|
| $C_2H_5$ | $C_2H_5$ | H | $(CH_3)_3N^{\oplus}CH_2CH_2Cl$ |
| $C_2H_5$ | $C_2H_5$ | H | $H_2N^{\oplus}(CH(CH_3)_2)_2$ |
| $C_2H_5$ | $C_2H_5$ | H | $H_2N^{\oplus}(CH_2CH_2OH)_2$ |
| $C_2H_5$ | $C_2H_5$ | H | $Na^{\oplus}$ |
| $CH_3$ | $CH_3$ | $CH_3$ | $(CH_3)_2N^{\oplus}$⟨ ⟩ (piperidinium) |
| $(CH_2)_5CH_3$ | H | H | $Na^{\oplus}$ |
| $C_2H_5$ | $CH_3$ | H | $(CH_3)_2N^{\oplus}$⟨ ⟩ (piperidinium) |
| $C_2H_5$ | $C_2H_5$ | H | $(CH_3)_2N^{\oplus}$⟨ ⟩ (piperidinium) |
| $C(CH_3)_3$ | H | H | $Na^{\oplus}$ |
| $C_2H_5$ | $CH_3$ | H | $Na^{\oplus}$ |
| $(CH_2)_2CH_3$ | $CH_3$ | $CH_3$ | $Na^{\oplus}$ |
| $C_2H_5$ | H | H | $Na^{\oplus}$ |
| $CH(CH_3)_2$ | H | H | $Na^{\oplus}$ |

TABLE B

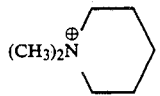

IB

| R¹ | R² | R³ | R |
|---|---|---|---|
| H | H | H | H |
| H | $CH_3$ | H | H |
| H | $CH_3$ | $CH_3$ | H |
| H | $C_2H_5$ | H | H |
| H | $C_2H_5$ | $CH_3$ | H |
| H | $C_2H_5$ | $C_2H_5$ | H |
| $CH_3$ | H | H | H |
| $CH_3$ | $CH_3$ | H | H |
| $CH_3$ | $CH_3$ | $CH_3$ | H |
| $CH_3$ | $C_2H_5$ | H | H |
| $CH_3$ | $C_2H_5$ | $CH_3$ | H |
| $CH_3$ | $C_2H_5$ | $C_2H_5$ | H |
| $C_2H_5$ | H | H | H |
| $C_2H_5$ | $CH_3$ | H | H |
| $C_2H_5$ | $CH_3$ | $CH_3$ | H |
| $C_2H_5$ | $C_2H_5$ | H | H |
| $C_2H_5$ | $C_2H_5$ | $CH_3$ | H |
| $C_2H_5$ | $C_2H_5$ | $C_2H_5$ | H |
| H | $CH_3$ | $CH_3$ | $Na^{\oplus}$ |

Specific examples of herbicidal benzothiadiazones II whose action can be improved by synergistic triazole compounds I, IA and IB are given in Table C:

TABLE C

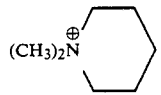

II

| No. | R⁴ | R⁵ | Literature |
|---|---|---|---|
| II.001 | H | H | DE-A 15 42 836 |
| II.002 | Cl | H | DE-A 24 44 383 |
| II.003 | F | H | DE-A 24 44 383 |
| II.004 | $CH_3$ | H | DE-A 24 43 901 |
| II.005 | H | $Na^{\oplus}$ | DE-A 15 42 836 |
| II.006 | Cl | $Na^{\oplus}$ | DE-A 24 44 383 |
| II.007 | F | $Na^{\oplus}$ | DE-A 24 44 383 |
| II.008 | $CH_3$ | $Na^{\oplus}$ | DE-A 24 43 901 |
| II.009 | Cl | CN | DE-A 26 56 289 |
| II.010 | F | CN | DE-A 26 56 289 |
| II.011 | $CH_3$ | CN | DE-A 26 56 289 |
| II.012 | H | CN | DE-A 26 56 289 |

For herbicidal benzothiadiazones of the formula II, the amount of synergistically active compound varies depending on the crop. The ratios may vary over a wide range, and are also dependent on the structure of the benzothiadiazones of the formula II and on the crop involved. Suitable ratios of synergistically active compound to herbicidal active ingredient are from 10:1 to 0.01:1, and particularly from 4:1 to 0.1:1, parts by weight.

The herbicidal active ingredients and synergistic compounds may be applied separately or together to the leaves and shoots of crop plants and undesired plants.

Preferably, the synergistic agent is applied simultaneously with the herbicidal active ingredient. The synergist and herbicidal active ingredient may be applied simultaneously but separately to the field, or one after the other. They may be formulated together or separately as suspensions, emulsions or solutions for use as spray liquors.

The amount of pure active ingredient required, i.e., without formulation auxiliaries, depends on the composition of the stand, the development stage of the plants, on local climatic conditions, and on the application technique employed. Generally, application rates are from 0.25 to 5, and preferably from 0.5 to 2.5, kg/ha.

The crops in which the herbicidal and synergistic agents may be used are essentially those in which the individual active ingredients of the mixture may be employed. In the case of agents containing benzothiadiazine derivatives of the formula II, examples of such crops are cereals, groundnuts, rice, soybeans, Indian corn, sorghum and peas.

The method of application is also important. If the novel agents are used for combating unwanted plants in crops having insufficient tolerance special techniques may be employed by means of which the leaves of the crop plants come as little into contact with the agents as possible, whereas the unwanted plants growing between or under the crop plants, or the free area between them, is hit by the agents post-directed or layby application.

The novel herbicidal agents may, in addition to the triazole derivative of the formula I. IA and/or IB as synergist and the herbicide from the group of benzothiadiazones II, contain further herbicidal and growth-regulating active ingredients and inert additives without the synergistic action being affected.

In addition to the synergistic action evident when the triazole compounds I, IA and IB are used together with benzothiadiazines of the formula II, they may also be used as synergists with the following herbicides trade names in brackets):

5-amino-4-chloro-2-phenylpyridazin-3(2H-one (Pyrazon) 4-chloro-5-methylamino-2-trifluoromethylphenyl-3(2H)-pyridazin-3(2H)-one (Monometfluorazon)

3-(3-chloro-4-methylphenyl-1,1-dimethylurea (Chlortoluron)

3-(4-bromophenyl-1-methoxy-1-methylurea (Metobromuron)

3-(4-isopropylphenyl)-1-dimethylurea (Isoproturon)

3(3,4-dichlorophenyl)1-methoxy-1-methylurea (Linuron)

3-(3,4-dichlorophenyl)-1,1-dimethylurea (Diuron)

3-(2-benzothiazolyl)-1,3-dimethylurea (Methabenzthiazuron)

1,1-dimethyl-3-(3-trifluoromethylphenyl)-urea (Fluometuron) methyl-2-[3-(4-methoxy-6-methyl-1,3,5-triazin-2-yl)aminocarbonylaminosulfonyl]benzoate) (Metsulfuron-methyl)

methyl-2-[3-(4,6-dimethoxypyrimidin-2-yl)aminocarbonylaminosulfonyl]-benzoate (Bensulfuron-methyl)

ethyl-2-[3-(4-chloro-6-methoxypyrimidin-2-yl)aminocarbonylaminosulfonyl]-benzoate (Chorimuron)

methyl-2-[3-(4-methoxy-6-methyl-1,3,5-triazin-2-yl)-3-methylaminocarbonylaminosulfonyl]benzoate 3-(4,6-dimethoxy-1,3,5-triazin-2-yl)-1-[2-(2-methoxyethoxy)phenylylsulfonyl]urea (Cinosulfuron)

methyl-2-[3-(4,6-bis(difluoromethoxy)pyrimidin-2-yl)-aminocarbonylaminosulfonyl[benzoate (Primisulfuron)

2-(2-chloroethoxy)N-[[(4-methoxy-6-methyl-1,3,5-triazin-2-yl)aminocarbonyl]benzenesulfonamide (Triasulfuron)

2-[[(4,6-dimethoxypyrimidin-2-yl)aminocarbonyl]aminosulfonyl]-3-pyridinecarboxylic acid-N,N-dimethylamide S-4-chlorobenzyl)-N,N-diethylthiocarbamate Benthiocarb)

S-benzyl-N,N-dipropylthiocarbamate (Prosulfocarb)

S-ethyl-N,N,-di-iso-butylthiocarbamate (Butylat)

S-ethyl-N,N-di-n-propylthiocarbamate (EFTC)

3-(methoxycarbonylamino)phenyl-N-(3-methylphenyl)carbamate (Phenmedipham)

3-ethoxycarbonylaminophenyl-N-phenylcarbamate (Desmedipham)

isopropyl-N-(3-chlorophenyl)-carbamate (Chloropropham)

2,6-dinitro-N,N-dipropyl-4-trifluoromethylaniline (Trifluralin)

3,4-dimethyl-2,6-dinitro-N-1-ethylpropylanilin (Pendimenthalin)

4-amino-3-methyl-6-phenyl-1,2,4-triazin-5(4H)-one (Metamitron)

4-amino-6-tert.-butyl-3-methylthio-1,2,4-triazin-5(4H)-one (Metribuzin)

2-(2-chloro-4-ethylamino-1,3,5-triazin-yl-amino)-2-methylpropionitrile Cyanazin)

2-chloro-4-ethylamino-6-iso-propylamino-1,3,5-triazlne (Atrazin)

2-chloro-4-ethylamino-6-tert.-butylamino-1,3,5-triazine (Terbutylazin)

3-chloro-4-chromethyl-1-(3-trifluoromethylphenyl)-pyrrolidin-2-one (Fluorochloridine)

2-chlor-6-nitro-3-phenoxyaniline (Aclonifen)

3,6-dichlor-2-methoxybenzoic acid (Dicamba)

2,5-dichloro-3-aminobenzoic acid (Amiben)

2,4-dichlorophenoxyacetic acid (2,4-D)

2-(2,4-dichlorophenoxy)propionic acid (Dichloprop)

2-(4-chloro-2-methylphenoxy)propionic acid (Mecoprop)

methyl-[4-(2,4-dichlorophenoxy)-phenoxy]propionate (Diclofop-methyl)

ethyl-2-[4-(6-chloro-2-benzoxazolyloxy)phenoxy]-propionate (Fenoxaprop-ethyl)

ethyl-2-[4-6-chloro-2-quinoxanyloxy)phenoxy]propionate (Quizalafop-ethyl)

methyl-2-[4-(3-chloro-5-trifluoromethyl-2-pyridyloxy)phenoxy]propionate (Haloxyfop-methyl)

butyl-2-[4-(5-trifluoromethyl-2-pyridyloxy)phenoxy]-propionate (Fluazifop-bentyl)

4-amino-3,5-dichloro-6-fluoro-2-pyridinyloxyacetic acid-1-methylheptyl ester (Fluroxypyr)

7-chlor-3-methylquinoline-8-carboxylic acid (Quinmerac)

3,7-dichloroquinoline-8-carboxylic acid (Quinchlorac)

N-(2,4-difluorophenyl)-2-(3-trifluoromethylphenoxy)-3-pyridincarboxamide (Diflufanican)

exo-1-methyl-4-(1-methylethyl)-2-(2-methylphenylmethoxy)-7-oxabicyclo (2.2.1)heptane (Cinmethlin)

2-)2-chlorophenyl)methyl-4,4-dimethyl-3-isoxazolidinon (Clomazon)

5-methylamino-2-phenyl-4-(3-trifluoromethylphenyl)furan-3(2H)-one (Flurtamon)

2-[4,5-dihydro-4-methyl-4-(1-methylethyl)-5-oxo-1H-imidazol-2-yl]-5-ethyl-3-pyridine carboxylic acid (Imazethapyr)

2-[4,5-dihydro-4-methyl-4-(1-methylethyl)-5-oxo-1H-imidazol-2-yl)-3-quinolinecarboxylic acid (Imazaquin)

4-choro-2-oxobenzothiazolin-3-ylacetic acid (Benazolin)

2-phenyl-3,1-benzoxazin-4-one 5-fluoro-2-phenyl-4H-3,1-benzoxazin-4-one (Fluorobentranie)

3′,4′-dichloropropionanilide (Propanil)

5-[2-chloro-4-(trifluoromethylphenoxy)]-2-nitrobenzoic acid, sodium salt (Acifluorfen)

methyl-5-2,4-dichlorophenoxy-2-nitrobenzoate (Bifenox)

5-2-chloro-4-trifluoromethylphenoxy)-2-nitro-N-methansulfonylbenzamide (Fomesafen)

3,5-dibromo-4-hydroxybenzonitrile (Bromoxynil)

3,5-diiodo-4-hydroxybenzonitrile (Ioxynil).

It may also be useful to apply the mixtures according to the invention in admixture with other crop protection agents, e.g. agents for combating pests or phytopathogenic fungi or bacteria. The mixtures may also be mixed with solutions of minerals used to remedy nutritional or trace element deficiencies.

The agents according to the invention, or the herbicidal active ingredient and the synergist when applied separately, may be applied for instance in the form of directly sprayable solutions, powders, suspensions including high-percentage aqueous oily or other suspensions), dispersions, emulsions, oil dispersions, pastes, dusts, broadcasting agents, or granules by spraying, atomizing dusting, broadcasting or watering. The forms of application depend entirely on the purpose for which the agents are being used.

The formulations contain from 0.1 to 95, and preferably from 0.5 to 90, wt % of active ingredient mixture, and may be produced by conventional methods.

For the preparation of solutions emulsions, pastes and oil dispersions to be sprayed direct, mineral oil fractions of medium to high boiling point. such as kerosene or diesel oil further coal-tar oils and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote as such or dissolved in an oil or solvent may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the herbicidal active ingredient and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide ground plastics fertilizers such as ammonium sulfate, ammonium phosphate, ammonium nitrate and ureas, and vegetable products such as grain flours bark meal wood meal, and nutshell meal, cellulosic powders, etc.

MANUFACTURING EXAMPLES

The directions given in the examples below were employed, after appropriate modification of the starting materials, for obtaining further compounds of the formulae I, IA and IB; the compounds obtained are listed with their physical data in Tables 1, 2 and 3 below.

Example 1

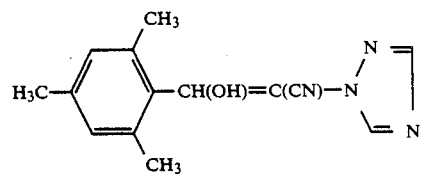

At 0° C. 60.6 g (0.54 mol) of potassium tert-butylate was added in portions to a mixture of 298.2 g (0.27 mol) of triazolyl acetonitrile, 49.3 g (0.27 mol) of 2,4,6-trimethylbenzoyl chloride and 250 mol of tetrahydrofuran. After the mixture had been stirred for 12 hours at 25° C., the solvent was stripped off under reduced pressure and the residue was taken up in water. This aqueous alkaline solution of the product was freed from impurities by extraction and then acidified, the product being obtained as a solid.

Yield: 44.4 g (65%); m.p. >200° C. Active ingredient no. 1.021.

Example 2

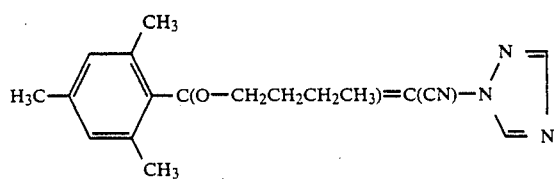

At 25° C., 11.0 g (0.08 mol) of butyl bromide was added to a suspension of 20.3 g (0.08 mol) of the product obtained in Example 1, 22.1 g (0.16 mol) of potassium carbonate and 100 ml of cyclopentanone, and the mixture obtained was stirred for 8 hours at 80° C. After cooling, the solids were separated off and the solution thus obtained was evaporated down under reduced pressure. After working up in a conventional manner, the product was purified by chromatography.

Yield: 14.2 g (57%); m.p.: 60°–70° C. Active ingredient No. 1.022.

Example 3

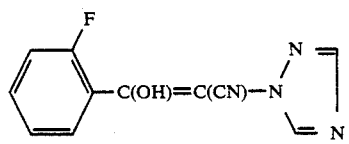

Analogously to Example 1, 62.7 g (74% of the desired product was obtained from 34.6 g (0.32 mol) of triazolyl acetonitrile and 50.7 (0.32 mol) of 2-fluorobenzoyl chloride in 250 ml of tetrahydrofuran with 71.8 g (0.64 mol) of potassium tert-butylate.

M.p.: 198°–201° C.; Active ingredient no. 1.002.

Example 4

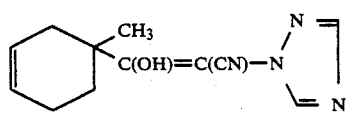

Analogously to Example 1, 18 g (27%) of the desired product was obtained from 30.2 g (0.28 mol) of triazolyl acetonitrile and 47.8 g (0.28 mol) of 1-methyl(bicyclo[2.2.1]hept-2-ene)carboxylic acid chloride (mixture of exo and endo isomers) in 250 ml of tetrahydrofurna with 69.0 g (0.62 mol) of potassium tert-butylate.

M.p.: 85°–88° C.; Active ingredient no. 2.041.

Example 5

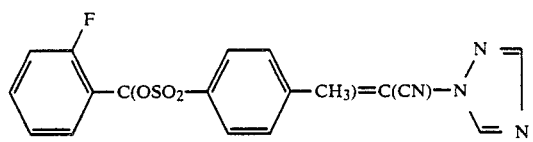

At 25° C. 0.1 g of N,N-dimethylaminopyridine and then 4.5 g (24 mmol) of p-toluenesulfonyl chloride were added to a solution of 5.0 g 22 mmol) of the product obtained according to Example 3 in 150 ml of tetrahydrofuran. The reaction mixture obtained was stirred for 3 hours at 70° C. and the solvent was then stripped off under reduced pressure. The product was obtained as a solid after a conventional working-up procedure.

Yield: 5.8 g (70%); m.p.: 111°–113° C.; Active ingredient no. 1.004.

Example 6

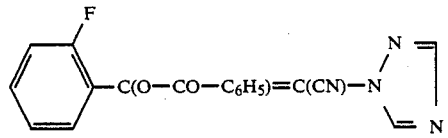

Analogously to Example 5, 2.8 g (40%) of the desired product was obtained as a solid from 5.0 g 22 mmol of the product obtained according to Example 3 with 3.4 g (24 mmol) of benzoyl chloride in 150 ml of tetrahydrofuran with 0.1 g of N,N-dimethylaminopyridine.

M.p.: 116°–118° C.; Active ingredient no. 1.003.

TABLE 1

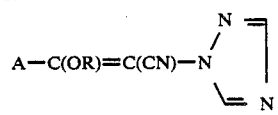

| No. | A | R | Phys. data mp (°C.); IR (cm$^{-1}$); $^1$H-NMR (δ in ppm) |
|---|---|---|---|
| 1.001 | phenyl | H | 141–142 |
| 1.002 | 2-F-phenyl | H | 198–201 |
| 1.003 | 2-F-phenyl | CO—C$_6$H$_5$ | 116–118 |
| 1.004 | 2-F-phenyl | SO$_2$—C$_6$H$_4$—CH$_3$ | 111–113 |
| 1.005 | 2-Cl-phenyl | H | 195–198 |
| 1.006 | 2-Cl-phenyl | n-C$_4$H$_9$ | 1630, 1503, 1433, 1321, 1172 |
| 1.007 | 2,4-Cl,Cl-phenyl | H | 210–212 |
| 1.008 | 2,4-Cl,Cl-phenyl | n-C$_4$H$_9$ | 81–85 |

TABLE 1-continued $$A-C(OR)=C(CN)-N\diagdown\underset{N}{\overset{N}{\diagdown}}\diagdown_N$$  I

| No. | A | R | Phys. data mp (°C.); IR (cm$^{-1}$); $^1$H-NMR (δ in ppm) |
|---|---|---|---|
| 1.009 | 2,4-Cl,Cl-phenyl | n-C$_6$H$_{13}$ | 64-66 |
| 1.010 | 2,4-Cl,Cl-phenyl | CH$_2$—C$_6$H$_5$ | 133-138 |
| 1.011 | 2,4-Cl,Cl-phenyl | CH$_2$CH=CH$_2$ | 90-92 |
| 1.012 | 2,6-Cl,Cl-phenyl | H | >190 |
| 1.013 | 2,6-Cl,Cl-phenyl | n-C$_3$H$_7$ | 1363, 1502, 1431 1311, 1174 |
| 1.014 | 2,6-Cl,Cl-phenyl | n-C$_4$H$_9$ | 89-101 |
| 1.015 | 2,6-Cl,Cl-phenyl | n-C$_5$H$_{11}$ | 1638, 1427, 1302 1230, 1148 |
| 1.016 | 2,6-Cl,Cl-phenyl | n-C$_6$H$_{12}$ | 2950, 2880, 2250, 1315, 1180 |
| 1.017 | 3,5-Cl,Cl-phenyl | H | 187-188 |
| 1.018 | 3,5-Cl,Cl-phenyl | n-C$_4$H$_9$ | 7.6(s,1H); 8.1(s,1H) |
| 1.019 | 3,5-Cl,Cl-phenyl | n-C$_5$H$_{11}$ | 2958, 1563, 1503, 1312, 1278 |
| 1.020 | 3,5-Cl,Cl-phenyl | n-C$_6$H$_{12}$ | 2957, 1563, 1313, 1278, 1172 |
| 1.021 | 2,4,6-trimethyl-phenyl | H | >200 |
| 1.022 | 2,4,6-trimethyl-phenyl | n-C$_4$H$_9$ | 60-70 |
| 1.023 | 2,4,6-trimethyl-phenyl | CH$_2$CH=CH$_2$ | 95-97 |
| 1.024 | 2,4,6-trimethyl-phenyl | Na$^\oplus$ | >200 |
| 1.025 | 4-Cl-phenyl | H | 192-195 |
| 1.026 | 2-CF$_3$-phenyl | n-C$_4$H$_9$ | 84-86 |
| 1.027 | 2-CH$_3$-phenyl | H | 199-202 |
| 1.028 | 2-CH$_3$-phenyl | Na$^\oplus$ | >200 |
| 1.029 | 2-CH$_3$-phenyl | n-C$_4$H$_9$ | 2962, 1624, 1503, 1317, 1278 |
| 1.030 | 2,4-CH$_3$,CH$_3$-phenyl | H | >190 |
| 1.031 | 2,4-CH$_3$,CH$_3$-phenyl | n-C$_3$H$_7$ | 51-54 |
| 1.032 | 2,4-CH$_3$,CH$_3$-phenyl | n-C$_5$H$_{11}$ | 92-96 |
| 1.033 | 2,4-CH$_3$,CH$_3$-phenyl | n-C$_6$H$_{13}$ | 63-69 |
| 1.034 | 2-F-phenyl | Na$^\oplus$ | >200 |
| 1.035 | 2-naphthyl | H | >200 |
| 1.036 | (CH$_2$)$_9$CH$_3$ | H | 72-75 |
| 1.037 | (CH$_2$)$_{14}$CH$_3$ | H | 82-84 |

TABLE 2

$$\underset{R^3}{\overset{R^1}{R^2-\underset{|}{\overset{|}{C}}-C(OR)=C(CN)-N}}\diagdown\underset{N}{\overset{N}{\diagdown}}\diagdown_N$$  IA

| No. | R$^1$ | R$^2$ | R$^3$ | R | Phys. data mp (°C.); IR (cm$^{-1}$); $^1$H-NMR (δ in ppm) |
|---|---|---|---|---|---|
| 2.001 | CH$_3$ | CH$_3$ | H | H | 78-80 |
| 2.002 | C$_2$H$_5$ | CH$_3$ | H | H | 87 |
| 2.003 | CH$_3$CH$_2$CH$_2$ | CH$_3$ | H | H | 2961, 2935, 1633, 1508 |
| 2.004 | (CH$_3$)$_2$CH | CH$_3$ | H | H | 117 |
| 2.005 | CH$_3$O | CH$_3$ | H | H | 117-118 |
| 2.006 | CH$_3$ | CH$_3$ | CH$_3$ | H | 2976, 1738, 1506, 1277 |
| 2.007 | C$_2$H$_5$ | CH$_3$ | CH$_3$ | H | 2973, 1736, 1505, 1278 |
| 2.008 | CH$_3$CH$_2$CH$_2$ | CH$_3$ | CH$_3$ | H | 2965, 1505, 1474, 1279 |
| 2.009 | HOCH$_3$ | CH$_3$ | CH$_3$ | H | [xHCl] 171-179 |
| 2.010 | CH$_3$OCH$_2$ | CH$_3$ | CH$_3$ | H | 2936, 1739, 1506, 1277 |
| 2.011 | CH$_3$CH$_2$OCH$_2$ | CH$_3$ | CH$_3$ | H | 1978, 1739, 1505, 1277, 1113 |
| 2.012 | CH$_3$CH$_2$CH$_2$CH$_2$OCH$_2$ | CH$_3$ | CH$_3$ | H | 1960, 1739, 1474, 1277 |
| 2.013 | C$_2$H$_5$ | C$_2$H$_5$ | H | H | 98-103 |
| 2.014 | CH$_3$CH$_2$CH$_2$CH$_2$ | C$_2$H$_5$ | H | H | 59-61 |
| 2.015 | C$_2$H$_5$ | C$_2$H$_5$ | CH$_3$ | H | 3112, 2969, 2207, 1520 |

TABLE 2-continued

IA $$R^2-\underset{R^3}{\overset{R^1}{C}}-C(OR)=C(CN)-N\begin{array}{c}N=\\|\\N\end{array}$$

| No. | R¹ | R² | R³ | R | Phys. data mp (°C.); IR (cm⁻¹); ¹H-NMR (δ in ppm) |
|---|---|---|---|---|---|
| 2.016 | CH₃CH₂CH₂ | n-C₃H₇ | H | H | 88-91 |
| 2.017 | H | —CH₂CH₂— | | H | 2209, 1592, 1508, 1277 |
| 2.018 | CH₃ | —CH₂CH₂— | | H | 152-156 |
| 2.019 | H | —CH₂CH₂CH₂— | | H | 2950, 1624, 1508, 1277 |
| 2.020 | H | —CH₂CH₂CH₂CH₂— | | H | 81-82 |
| 2.021 | H | —CH₂CH₂CH₂CH₂CH₂— | | H | 121-125 |
| 2.022 | CH₃ | —CH₂CH₂CH₂CH₂CH₂— | | H | 2935, 1504, 1277, 1134 |
| 2.023 | H | 1-adamantyl | H | H | 114-117 |
| 2.024 | C₂H₅ | C₂H₅ | H | COCH₃ | 2970, 1757, 1505, 1205 |
| 2.025 | C₂H₅ | C₂H₅ | H | COC₂H₅ | 2867, 1785, 1506, 1087 |
| 2.026 | C₂H₅ | C₂H₅ | H | CO—C₆H₅ | 2970, 1757, 1505, 1205 |
| 2.027 | C₂H₅ | C₂H₅ | H | CO—C₆H₄—Cl (4-Cl) | 1758, 1593, 1204, 1089 |
| 2.028 | C₂H₅ | C₂H₅ | H | CO—C₆H₃(2-Cl)(4-CH₃) | 2967, 1770, 1585, 1201 |
| 2.029 | CH₃ | C₂H₅ | H | COCH₃ | 2970, 2937, 2217, 1633 |
| 2.030 | CH₃ | CH₃ | CH₃ | SO₂CH₃ | 1362, 1187, 1088, 795 |
| 2.031 | H | CH₃ | C₂H₅ | SO₂CH₃ | 60-65 |
| 2.032 | H | CH₃ | C₂H₅ | SO₂—C₆H₂(2,6-(CH₃)₂)(4-CH₃) | 1371, 1176, 1210, 1053 |
| 2.033 | H | CH₃ | i-C₃H₇ | SO₂—C₆H₄—CH₃ (4-CH₃) | 30-40 |
| 2.034 | H | C₂H₅ | C₂H₅ | SO₂CH₃ | 1506, 1372, 1210, 1177 |
| 2.035 | H | C₂H₅ | C₂H₅ | SO₂—C₆H₄—CH₃ (4-CH₃) | 78-87 |
| 2.036 | H | C₂H₅ | C₂H₅ | SO₂—C₆H₂(2,6-(CH₃)₂)(4-CH₃) | 2968, 1054, 1370, 1175 |

TABLE 2-continued $$R^2-\underset{\underset{R^3}{|}}{\overset{\overset{R^1}{|}}{C}}-C(OR)=C(CN)-N\diagdown\text{(triazole)}$$

IA

| No. | R¹ | R² | R³ | R | Phys. data mp (°C.); IR (cm⁻¹); ¹H-NMR (δ in ppm) |
|---|---|---|---|---|---|
| 2.037 | H | $C_2H_5$ | $C_2H_5$ | 4-Br-C₆H₄-SO₂- | 108–114 |
| 2.038 | H | $C_2H_5$ | $C_2H_5$ | 2-CH₃-4-Cl-C₆H₃-SO₂- | 112–116 |
| 2.039 | H | $C_2H_5$ | $C_2H_5$ | 2,4,5-Cl₃-C₆H₂-SO₂- | 137–139 |
| 2.040 | H | $C_2H_5$ | $C_2H_5$ | 2,6-Cl₂-C₆H₃-SO₂- | 100–104 |
| 2.041 | CH₃ | (3-ethyl-cyclopent-2-enyl) | | H | 85–88 |
| 2.042 | H | H | H | H | 155 |
| 2.043 | CH₃ | H | H | H | 134–136 |
| 2.044 | CH₂CH₃ | H | H | H | 108 |
| 2.045 | CH(CH₃)₂ | H | H | H | 126 |
| 2.046 | C(CH₃)₃ | H | H | H | 143 |
| 2.047 | (CH₂)₅CH₃ | H | H | H | 61–63 |
| 2.048 | CH₂CH₃ | CH₂CH₃ | H | (CH₃)₂N⊕CH₂CH₂Cl | 8.50(s,1H); 7.85(s,1H) |
| 2.049 | CH₂CH₃ | CH₂CH₃ | H | H₂N⊕(CH(CH₃)₂)₂ | 2962, 2170, 1539, 1275 |
| 2.050 | CH₂CH₃ | CH₂CH₃ | H | H₂N⊕(CH₂CH₂OH)₂ | 2961, 2175, 1537, 1457 |
| 2.051 | CH₂CH₃ | CH₂CH₃ | H | Na⊕ | 95–100 |
| 2.052 | CH₃ | CH₃ | CH₃ | N-(CH₃)₂-piperidinium | 2951, 2151, 1533, 1480 |
| 2.053 | (CH₂)₅CH₃ | H | H | Na⊕ | 67–70 |
| 2.054 | CH₂CH₃ | CH₃ | H | N-(CH₃)₂-piperidinium | 8.45(s,1H); 8.15(s,1H) |
| 2.055 | CH₂CH₃ | CH₂CH₃ | H | N-(CH₃)₂-piperidinium | 8.45(s,1H); 8.15(s,1H) |
| 2.056 | C(CH₃)₃ | H | H | Na⊕ | >200 |
| 2.057 | CH₂CH₃ | CH₃ | H | Na⊕ | 130–140 |

TABLE 2-continued $$R^2-\overset{\overset{R^1}{|}}{\underset{\underset{R^3}{|}}{C}}-C(OR)=C(CN)-N\overset{N=}{\underset{N}{\diagdown}}\qquad \text{IA}$$

| No. | $R^1$ | $R^2$ | $R^3$ | R | Phys. data mp (°C.); IR (cm$^{-1}$); $^1$H-NMR ($\delta$ in ppm) |
|---|---|---|---|---|---|
| 2.058 | (CH$_2$)$_2$CH$_3$ | CH$_3$ | CH$_3$ | Na$^\oplus$ | 132–133 |
| 2.059 | CH$_2$CH$_3$ | H | H | Na$^\oplus$ | 114–121 |
| 2.060 | CH(CH$_3$)$_2$ | H | H | Na$^\oplus$ | >200 |

TABLE 3

$$\underset{R^3}{\overset{R^2}{\diagdown}}C=C(R^1)-C(OR)=C(CN)-N\overset{N=}{\underset{N}{\diagdown}}\qquad \text{IB}$$

| No. | $R^1$ | $R^2$ | $R^3$ | R | Phys. data mp (°C.); IR (cm$^{-1}$); $^1$H-NMR ($\delta$ in ppm) |
|---|---|---|---|---|---|
| 3.001 | H | CH$_3$ | CH$_3$ | H | 118 |
| 3.002 | CH$_3$ | CH$_3$ | H | H | 64–71 |
| 3.003 | C$_2$H$_5$ | CH$_3$ | H | H | 81–88 |
| 3.004 | H | CH$_3$ | CH$_3$ | Na$^\oplus$ | >200 |

USE EXAMPLES

The synergistic action of the triazole compounds of the formulae I, IA and IB is illustrated by greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 5 cm before being treated with emulsions or suspensions of the active ingredients in water. In this treatment method, either plants which had been sown in the pots and grown there were selected, or they were cultivated separately as seedlings and transplanted to the pots a few days before being treated. The application rates for postemergence treatment were 0.125 to 1.5 kg/ha. No covers were placed on the vessels in this method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants employed for the experiments were Amaranthus retroflexus and Glycine max.

The following active ingredients, or mixtures containing them, were used:

Active ingredient no. II.005 was employed as representative of the benzothiadiazones II

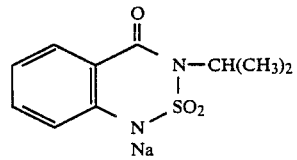

II.005

The active ingredient was formulated as an aqueous solution in a concentration of 480 g/l.

Active ingredient no. 1.002 was used as a representative of the synergistic triazole compounds I, and active ingredient no. 2.041 as representative of the triazole compounds IA. Both triazole compounds were formulated as 10% emulsion concentrates in a mixture consisting of 70% of solvent, 20% of emulsifier and 10% of surfactant.

Additionally, all formulations contained surfactant additives and 11.2 l/ha of ammonium nitrate/urea solution (28% nitrogen).

In these examples the method of S.R. Colby Weeds (15,20) was used to calculate the value E which is to be expected if the combined action of the individual components of the mixture is merely additive.

The formula employed is $$E = X + Y - \frac{XY}{100}$$

where x is the percentage action with preparation A at concentration a; y is the percentage action with preparation B at concentration b; and E is the expected action (in %) of A+B at application rates a+b.

TABLE 1

| Synergistic herbicidal action of the mixture according to the invention consisting of the triazole derivative 1.002 and the herbicide II.005 | | | |
|---|---|---|---|
| Herbicide No. II.005 kg/ha | Example No. 1.002 kg/ha | Test plants and damage in % (E) | |
| | | Glycine max. | Amaranthus retrofl. |
| 0.625 | — | 2 (—) | 45 (—) |
| 1.25 | — | 0 (—) | 55 (—) |
| — | 0.125 | 0 (—) | 0 (—) |
| — | 0.25 | 0 (—) | 0 (—) |
| 0.625 | 0.125 | 5 (2)* | 100 (45) |
| 0.625 | 0.25 | 0 (2)* | 98 (45) |
| 1.25 | 0.25 | 8 (0) | 100 (55) |

(*) antagonistic effect

TABLE 2

Synergistic herbicidal action of the mixture according to the invention consisting of the triazole derivative 2.041 and the herbicide II.005

| Herbicide No. II.005 kg/ha | Example No. 2.041 kg/ha | Test plants and damage in % (E) | |
|---|---|---|---|
| | | Glycine max | Amaranthus retrofl. |
| 0.313 | — | 2 (—) | 35 (—) |
| 0.625 | — | 2 (—) | 45 (—) |
| 1.25 | — | 0 (—) | 55 (—) |
| — | 0.125 | 0 (—) | 0 (—) |
| — | 0.25 | 0 (—) | 0 (—) |
| 0.313 | 0.125 | 0 (2)* | 80 (35) |
| 0.313 | 0.25 | 0 (2)* | 98 (35) |
| 0.625 | 0.125 | 0 (2)* | 95 (45) |
| 1.25 | 0.125 | 8 (0) | 100 (55) |
| 1.25 | 0.25 | 8 (0) | 100 (55) |

(*) antagonistic effect

We claim:

1. A triazole compound of the formula I

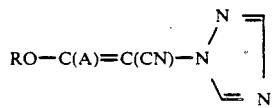

where A is $C_7-C_{20}$-alkyl, phenyl, naphthyl or pyridyl, or one of these aromatic radicals carrying from one to five halogen atoms, a phenyl or phenoxy radical or one to three hydroxy, nitro, amino, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio radicals or is phenyl carrying a mixture of halogen and $C_1-C_4$-alkyl;

R is hydrogen; $C_1-C_6$-alkyl, $C_3-C_6$-alkenyl or $C_3-C_6$-alkynyl, or one of these groups carrying from one to five halogen atoms, or a $C_1-C_4$-alkoxy, $C_1-C_4$-haloalkoxy, $C_1-C_4$-alkylthio, $C_1-C_4$-haloalkylthio or phenyl radical; or is a radical $COR^x$ or a radical $SO_2R^x$, where $R^x$ is hydrogen, $C_1-C_8$-alkyl which may carry from one to three halogen atoms, or phenyl which may carry from one to five halogen atoms or from one to three $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio radicals, and environmentally compatible salts thereof.

2. A triazole compound of the formula I as set forth in claim 1, A denoting phenyl which is unsubstituted or mono- to trisubstituted by halogen, $C_1-C_4$ alkyl or $C_1-C_2$-haloalkyl or a mixture of halogen and $C_1-C_4$-alkyl.

* * * * *